United States Patent

Dorsel et al.

Patent Number: 5,719,673
Date of Patent: Feb. 17, 1998

[54] INTERFEROMETER ARRANGEMENT WITH ADJUSTABLE OPTICAL PATH LENGTH DIFFERENCE FOR DETECTING A DISTANCE BETWEEN DIFFERENT LAYERS OF AN EYE

[75] Inventors: Andreas Dorsel, Menlo Park, Calif.; Karl-Heinz Donnerhacke, Jena, Germany; Beate Moeller, Jena, Germany; Guenter Maschke, Jena, Germany

[73] Assignee: Carl Zeiss Jena GmbH, Jena, Germany

[21] Appl. No.: 599,083

[22] Filed: Feb. 9, 1996

[30] Foreign Application Priority Data

Feb. 10, 1995 [DE] Germany ............... 195 04 444.4

[51] Int. Cl.⁶ ................................. G01B 9/02
[52] U.S. Cl. .............. 356/345; 250/237 G; 250/358
[58] Field of Search ............... 356/345, 349, 356/356, 358, 359, 360; 250/237 G

[56] References Cited

U.S. PATENT DOCUMENTS

| | | |
|---|---|---|
| 5,321,501 | 6/1994 | Swanson et al. ............... 356/345 |
| 5,402,230 | 3/1995 | Tian et al. |
| 5,486,918 | 1/1996 | Nagashima ............... 356/237 G |
| 5,523,838 | 6/1996 | Nagashima |
| 5,576,834 | 11/1996 | Hamada |

FOREIGN PATENT DOCUMENTS

| | | |
|---|---|---|
| 478801A1 | 4/1992 | European Pat. Off. |
| 2255633 | 11/1992 | United Kingdom |

*Primary Examiner*—Frank G. Font
*Assistant Examiner*—Robert Kim
*Attorney, Agent, or Firm*—McAulay Fisher Nissen Goldberg & Kiel, LLP

[57] ABSTRACT

An interferometer arrangement has an adjustable optical path length difference in at least one interferometer arm and a photoelectric receiver for detecting the interference signals generated by the interferometer. An incremental grating transmitter is coupled to the arrangement with a device for changing the optical path length difference and for generating a reference signal which changes its frequency like that of the interference signal depending on the rate of change of the optical path difference.

10 Claims, 3 Drawing Sheets

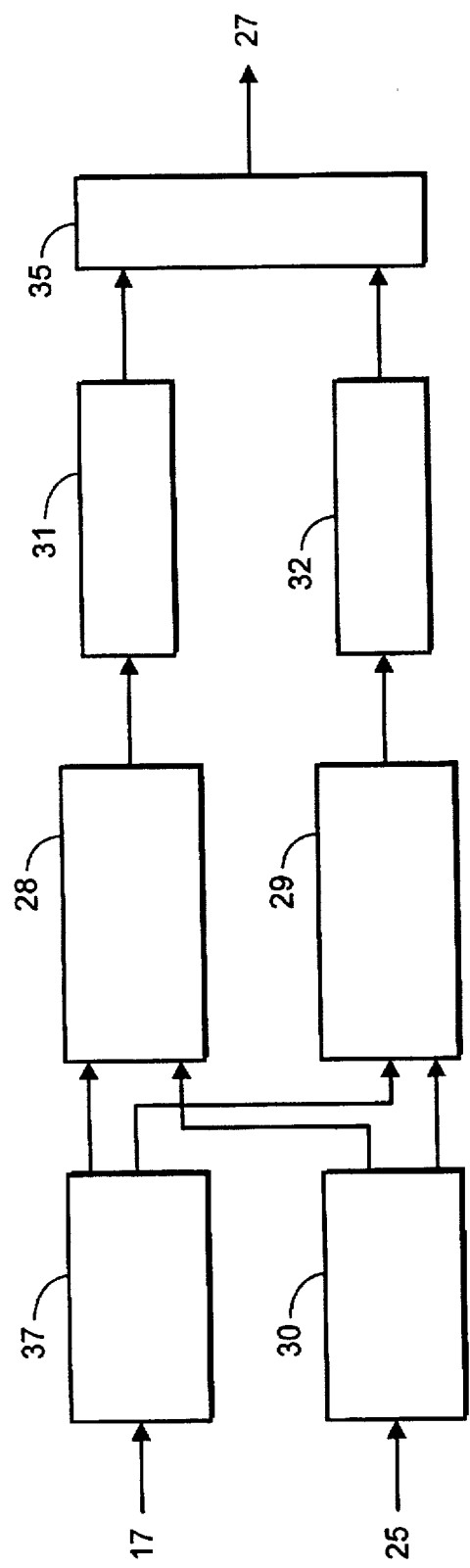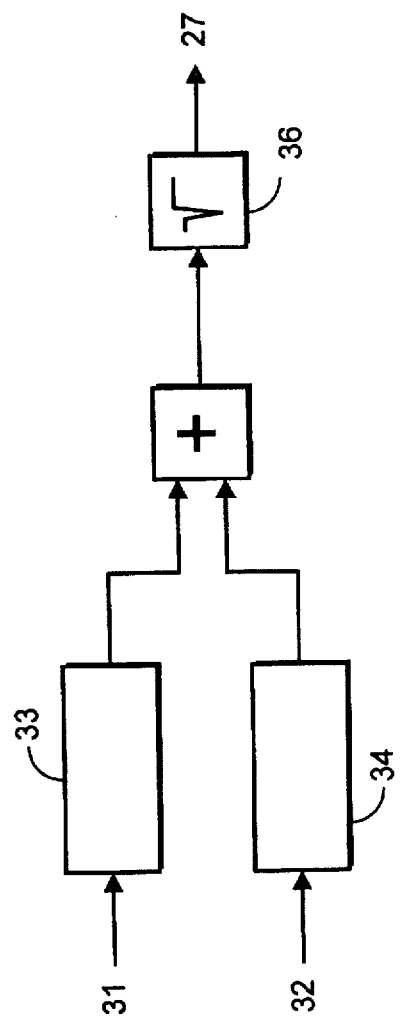

INTERFEROMETER ARRANGEMENT WITH ADJUSTABLE OPTICAL PATH LENGTH DIFFERENCE FOR DETECTING A DISTANCE BETWEEN DIFFERENT LAYERS OF AN EYE

BACKGROUND OF THE INVENTION a) Field of the Invention

The invention is directed to an interferometer arrangement with adjustable optical path length difference.

b) Description of the Related Art

It is already known (DE 3201801), for example, to combine in an observation beam the light from a light source of short coherent length which is reflected by a first interface or boundary surface of the eye with the light reflected by another boundary surface via an interferometric arrangement, the difference in the optical path lengths between the reflected light components being compensated for via a displaceable mirror. For this purpose, the displacement of the mirror represents the measurement for the distance between the boundary surfaces analyzed.

Further, it is known, for example, from "Lasers in Surgery and Medicine" 13, 447–452 (1993), to direct an illuminating beam onto the eye, e.g., by means of a laser diode, via an interferometric arrangement with an adjustable difference in path lengths between the interferometric partial beams and to detect the interference contrast of the occurring interference of the beam components reflected by the eye by means of a photodetector arrangement depending on the adjustment of the difference in path length. The adjustment of the difference in path length is effected by means of a reflector, e.g., a triple prism, which is displaceable in an interferometer arm by means of a motor. Due to the low reflectivity of the boundary surfaces to be measured, the intensity of the interference signals to be detected is very low and noise is superimposed thereupon. The measurement signal should now be detected selectively. If the displaceable reflector is moved at a velocity v, the measurement signal to be detected has a frequency $f_s=2v/\lambda$ and is amplitude-modulated in accordance with the coherence length of the light source, where $\lambda$ represents the wavelength of the short-coherence light source.

The known and obvious solution, namely to select the measurement signal through the use of narrow-band electronic filters, is impeded by fluctuations in the velocity at which the optical path difference in the interferometer changes and accordingly at which the signal frequency $f_s$ changes. Also, as a result of temporary fluctuations in velocity, the signal frequency lies outside the bandwidth of the filter and the measurement signal is detected erroneously or not at all.

A high-precision regulation of the motor drive which, for example, drives a triple prism for adjusting the optical path length difference is very costly when the required constancy of the velocity is to be ensured also in the range of relatively high frequency components (100 Hz or more).

OBJECT AND SUMMARY OF THE INVENTION

For the above reasons, the primary object of the present invention is to obtain an uncorrupted signal in an economical manner.

In accordance with the invention, in an interferometer arrangement with adjustable optical path length difference in at least one interferometer arm and a first photoelectric receiver for detecting the interference signals generated by the interferometer, the improvement comprises an incremental transmitter coupled to the arrangement with means for changing the optical path length difference and for generating a reference signal which changes its frequency like that of the interference signal depending on the rate of change of the optical path length difference.

By means of a grating transmitter, a reference signal is derived directly from the movement of the mirror or retroreflector that is moved in order to change the difference in the optical paths. As a result of a suitably designed grating transmitter, for example, the period of this reference signal advantageously has the same value as that of the measurement signal.

Since the grating transmitter directly detects the change in the difference of path length in the interferometer, fluctuations in velocity act on the reference frequency and on the frequency of the measurement signal in like manner. Thus, the reference frequency can be used for demodulating the measurement signal. However, since the phase position of the measurement signal with respect to the reference signal is not known, it is not possible to utilize a demodulator in the usual sense. Rather, an arrangement is used for demodulation in two channels with a 90-degree phase displacement and subsequent coordinate transformation. The period of the grating transmitter (scale grating) can also be a multiple or a fraction of the signal frequency. In this case, a reference signal is generated at the same frequency as the measurement signal by means of electronic interpolation or division. However, the period of the grating transmitter signal should be smaller than the period of the changes in velocity so that these changes may be detected in their entirety.

In the case of a mirror or retroreflector moving along the beam in the interferometer, a period of the measurement signal corresponds to half the mean wavelength of the light of the short-coherence light source. In this case, it is advantageous to use an interferometric grating transmitter whose signal period likewise amounts to a half wavelength.

This is made possible by a grating transmitter whose grating constant G is equal to the mean wavelength of the short-coherence light source and at which the interference of the +1st order and −1st order can be effected. The frequency $f_g$ of the grating transmitter signal is then given by $f_g=2v/G$, where v designates the movement velocity.

Since the mean wavelength varies in an exemplary manner under certain cicumstances, it may be advisable to use a grating transmitter with a grating constant corresponding to the shortest anticipated mean wavelength and, for other wavelengths, to rotate the entire grating transmitter (e.g., in a two-grating transmitter, the reference grating and the scale grating) in the opposite direction in relation to the movement direction. In this case, the dimensioning of the scale grating must be sufficient to prevent wandering out of the ruled region.

Naturally, multiple-grating transmitters can also be used. The use of opaque grating transmitters is particularly advantageous, but transparent grating transmitters can also be used.

The signal can also be evaluated in other ways, e.g., by a digital computing device. For example, the reference signal and measurement signal can first be digitized and the phase-sensitive rectification in two channels at a 90-degree phase displacement and mediation (low-pass filter) with subsequent coordinate transformation from Cartesian to polar coordinates is then realized by a digital computing device. Another possibility consists in carrying out only the coordinate transformation by means of a digital computing device.

Other results and advantages of the invention are described more fully in the following with reference to the schematic drawings.

BRIEF DESCRIPTION OF THE DRAWINGS

FIGS. 3a and 3b show the construction of an arrangement for demodulation in two channels which are offset by 90° with subsequent coordinate transformation.

DESCRIPTION OF THE PREFERRED EMBODIMENTS

Figure 1:
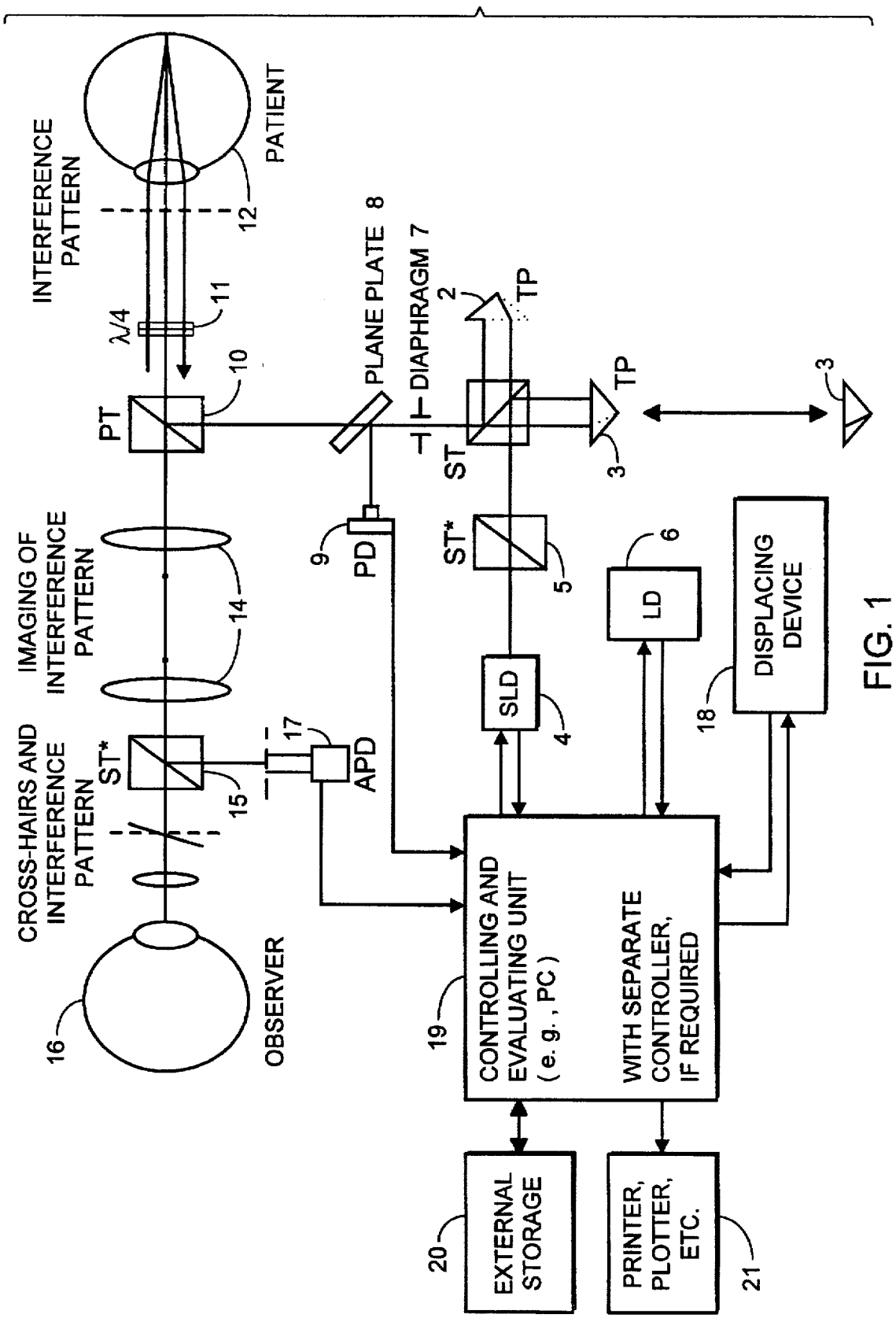
FIG. 1 shows an interferometer construction for measuring the distance between different layers in the human eye.

A beam splitter 1, together with a triple prism 2 and a displaceable triple prism 3, form an interferometer arrangement into which is beamed the light of a superluminescent diode 4 or laser diode 6, optionally, as measurement light source or adjustment light source, respectively.

Via a diaphragm 7 and a plane plate 8 for cutting out a control component on a photodiode 9, the illumination light strikes the eye 12 via a polarizing beam splitter 10 and a v/4-plate 11.

The light reflected by the eye is imaged, via a polarizing beam splitter 10 and an imaging system 14, in an observation plane or on a photodetector 17, preferably an avalanche photodiode, via a beam splitter 15.

The light sources 4 and 6, a displacing device 18 for displacing the triple prism 3, and the photodetectors 9, 17 are coupled with a controlling and evaluating unit 19 which can be connected in turn to external storages 20 and printers 21.

Figure 2:
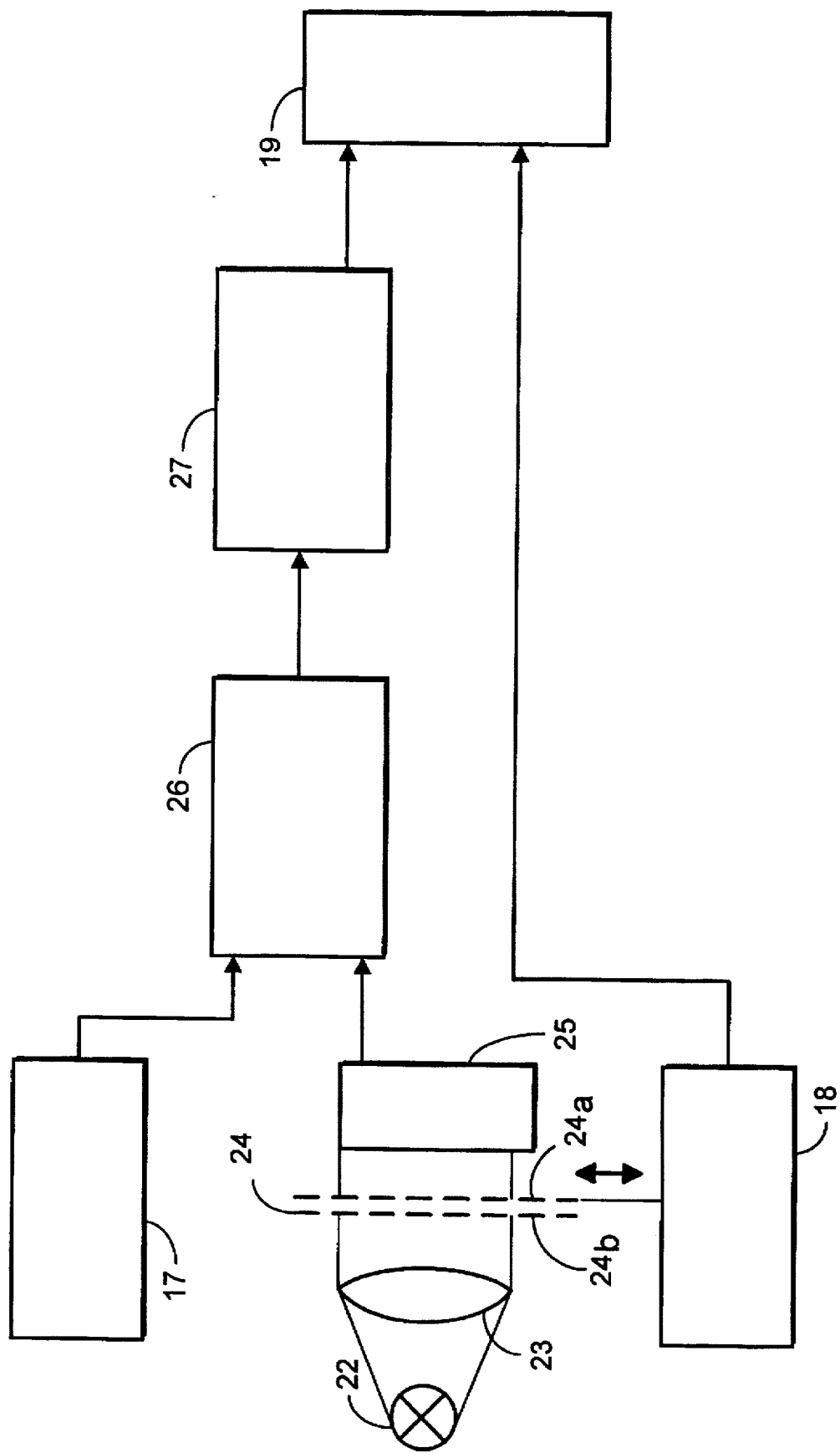
FIG. 2 shows an evaluating circuit according to the invention.

The elements essential to the invention are shown schematically in FIG. 2. A grating transmitter 24 which is rigidly coupled with the displacing device 18 with respect to its movable scale grating is associated with another laser diode 22. The light of the laser diode 22 is expanded by means of a collimator 23 and strikes a grating transmitter 24 as a bundle of parallel beams, the grating transmitter 24 being formed of a scale grating 24a, which is movable by means of the displacing device, and a stationary reference grating 24b.

The occurring light-dark signal arrives at a photoelectric receiver 25 (photodiode) with an integrated amplifier. The reference signal occurring at the receiver 25 is a sine-wave signal of the same frequency as the measurement signal which occurs at the output of the receiver preamplifier of the APD 17 with superimposed noise.

The two signals arrive at an arrangement 26 for demodulation in two channels at a 90-degree phase displacement with subsequent coordinate transformation which produces the envelope of the amplitude-modulated measurement signal which is proportional to the interference contrast.

The output signal of the arrangement for demodulation in two channels at a 90-degree phase displacement with subsequent coordinate transformation is fed to an A-D converter 27 and is stored after digitization in the PC 19. The signal generated by the incremental transmitter of the motor of the displating device 18 is likewise fed to the PC so that the envelope of the measurement signal can be represented as a function of the displacement location. The signal from the grating transmitter is also advantageously used for plotting the displacement location.

FIG. 3a shows a particularly advantageous manner of functioning of the arrangement for demodulating in two channels which are phase-offset by 90° with subsequent coordinate transformation. The measurement signal, with superimposed noise, from the APD 17 passes through a broad-band amplifier 37 and arrives at an input of two double-balancing mixers (DBM) 28 and 29 in each instance. The reference signal from the receiver 25 arrives at a broad-band phase shifter 30 which generates two phase-quadrature signals (sine and cosine) which likewise arrives at an input of the double-balancing mixer 28 and 29 in each instance.

When two sinusoidal or square-wave signals which are phase-offset by 90° are generated by the grating transmitter, these signals can be fed directly to the DBM 28, 29 without a phase shifter. The input signals are mixed, i.e., multiplied or rectified in a phase-sensitive manner, in the DBM 28, 29. The output signals of the DBM 28, 29 are freed from the residual carrier frequency via low-pass filters 31, 32. The signals occurring downstream of the low-pass filters 31, 32 pass through squaring means 33, 34, according to FIG. 3b, whose signals are combined and accordingly added. The sum of the squared signals can be transmitted to a square-root element. The occurring output signal is the envelope of the measurement signal of the APD and is sent to the A-D converter according to FIG. 2.

The computer 19 controls the switching on of the light sources 4 and 6 and the movement of the motor of the displacing device 18, the digitized values being detected and imaged at the same time.

While the foregoing description and drawings represent the preferred embodiments of the present invention, it will be obvious to those skilled in the art that various changes and modifications may be made therein without departing from the true spirit and scope of the present invention.

What is claimed is:

1. In an interferometer arrangement with adjustable optical path length difference for detecting a distance between different layers of the eye by means of a short-coherent light source, with a displaceable or adjustable optical path length difference in at least one interferometer arm and a first photoelectric receiver for detecting the interference signals generated by the interferometer, wherein an incremental transmitter is coupled with means for changing the optical path length difference and generates a reference signal which changes its frequency like that of the interference signal depending on the rate of change of the optical path length difference.

2. The interferometer arrangement according to claim 1, including a displacing unit for changing the optical path length difference, said displacing unit being rigidly connected with a movable scale grating of said transmitter which is located in the beam path of a light source and to which is associated a second photoelectric receiver, the first and second photoelectric receivers being connected with an evaluating unit.

3. The interferometer arrangement according to claim 2, wherein at least the evaluating unit is connected with a computer.

4. The interferometer arrangement according to claim 1, wherein said transmitter has an output signal having the same period as the interference signal.

5. The interferometer arrangement according to claim 1, wherein said transmitter is a grating transmitter having a movable grating with a grating constant, the grating constant corresponding approximately to the measured wavelength, where the interference of the −1st and +1st order is detected.

6. The interferometer arrangement according to claim 1, wherein the measurement signal generated by the first photoelectric receiver and the reference signal generated by the second photoelectric receiver arranged downstream of the grating transmitter are supplied to an arrangement for demodulating in two channels which are phase-offset by 90° with subsequent coordinate transformation, said demodulating arrangement being connected with an evaluating computer via an A-D converter.

7. The interferometer arrangement according to claim 6, wherein the arrangement for demodulating in two channels which are phase-offset by 90°, with subsequent coordinate transformation, has a first and a second multiplicative mixer, the reference signal for said mixers being formed of a first and second component with a 90-degree difference in phase, the first component being provided to an input of the first multiplicative mixer and the second component being provided to an input of the second multiplicative mixer, the measurement signal being provided to the other respective input of the mixer via a broad-band amplifier and the signals of the multiplicative mixers being supplied to the A-D converter via low-pass filters and an arrangement for coordinate transformation from Cartesian coordinates to polar coordinates.

8. The interferometer arrangement according to claim 6, wherein a broad-band 90-degree phase shifter is arranged upstream of the multiplicative mixers.

9. The interferometer arrangement according to claim 7, wherein the arrangement for coordinate transformation is formed of two squaring devices whose signals are combined and fed to a square-root element.

10. The interferometer arrangement according to claim 7, wherein the multiplicative mixer is a double-balancing mixer.

* * * * *